(12) United States Patent
Loupas et al.

(10) Patent No.: US 11,635,514 B2
(45) Date of Patent: *Apr. 25, 2023

(54) IMAGING METHODS AND APPARATUSES FOR PERFORMING SHEAR WAVE ELASTOGRAPHY IMAGING

(71) Applicant: SUPERSONIC IMAGINE, Aix en Provence (FR)

(72) Inventors: Thanasis Loupas, Psychico (GR); Matthew Frederick Bruce, Les Milles (FR); Aline Laure Criton, Boulogne Billancourt (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 75 days.

This patent is subject to a terminal disclaimer.

(21) Appl. No.: 16/947,646

(22) Filed: Aug. 11, 2020

(65) Prior Publication Data

US 2020/0371232 A1 Nov. 26, 2020

Related U.S. Application Data

(62) Division of application No. 15/522,512, filed as application No. PCT/IB2014/002600 on Oct. 28, 2014, now Pat. No. 10,775,499.

(51) Int. Cl.
*G01S 15/89* (2006.01)
*A61B 8/08* (2006.01)
*G01S 7/52* (2006.01)

(52) U.S. Cl.
CPC .......... *G01S 15/8915* (2013.01); *A61B 8/08* (2013.01); *A61B 8/485* (2013.01); *A61B 8/5276* (2013.01); *G01S 7/52022* (2013.01); *G01S 7/52042* (2013.01); *G01S 7/52071* (2013.01); *G01S 15/8979* (2013.01); *A61B 8/488* (2013.01); *G01N 2291/02827* (2013.01)

(58) Field of Classification Search
CPC .......... A61B 9/08; A61B 8/485; A61B 8/488; A61B 8/5276; G01S 7/52042; G01S 7/52071; G01S 7/52022; G01S 15/8979; G01S 15/8915; G01N 2291/02827
See application file for complete search history.

(56) References Cited

U.S. PATENT DOCUMENTS 9,320,491 B2 * 4/2016 Konofagou ............ A61B 8/467
11,138,723 B2 * 10/2021 Honjo ..................... G06T 7/11
(Continued)

FOREIGN PATENT DOCUMENTS

JP 2013-078675 A 5/2013
WO 2014-136502 A1 2/2017
WO WO-2018130503 A1 * 7/2018 ............. A61B 8/085

OTHER PUBLICATIONS

U.S. Appl. No. 15/522,512, filed Apr. 27, 2017.

*Primary Examiner* — Natalie Huls
(74) *Attorney, Agent, or Firm* — Nixon & Vanderhye (57) ABSTRACT

A method for performing shear wave elastography imaging of an observation field in a medium, the method comprising a plurality of shear wave imaging steps (30) to acquire a plurality of sets of shear wave propagation parameters, the method further comprising a reliability indicator determining step (40) during which a reliability indicator of the shear wave elastography imaging of the observation field is determined.

26 Claims, 3 Drawing Sheets

(56) References Cited

U.S. PATENT DOCUMENTS

| | | | |
|---|---|---|---|
| 11,471,130 B2* | 10/2022 | Bini | A61B 8/485 |
| 2015/0173718 A1 | 6/2015 | Tabaru et al. | |
| 2021/0007712 A1* | 1/2021 | Fuse | A61B 8/5207 |
| 2022/0104794 A1* | 4/2022 | De Beni | G06N 20/00 |

* cited by examiner

IMAGING METHODS AND APPARATUSES FOR PERFORMING SHEAR WAVE ELASTOGRAPHY IMAGING

FIELD OF THE INVENTION

The present invention relates to imaging methods and apparatuses for performing shear wave elastography imaging of an observation field in a medium.

BACKGROUND OF THE INVENTION

U.S. Pat. No. 7,252,004 describes an example of a shear wave elastography method for imaging an observation field in a medium.

While the method of U.S. Pat. No. 7,252,004 gives full satisfaction when tissue motion in the medium is limited, the reproducibility and reliability of images and measurements may not be optimal when tissues undergo stronger motion.

For instance shear wave elastography performed in the liver and abdomen can be sensitive to small movements due to the breathing of the patient, to shadowing from the lungs ribs and intervening tissues, or even to pulsation of the organs linked to heart rate.

There is thus a need for a method for performing shear wave elastography imaging of an observation field in a medium that could provide reduced measurement variability, shorten acquisition times or reduce the number of failed acquisitions.

Such a method can be particularly useful for new users since it can reduce the learning curve of shear wave elastography imaging.

SUMMARY OF THE INVENTION

To this aim, a first object of the invention, is a method for performing shear wave elastography imaging of an observation field in a medium, the method comprising a plurality of shear wave imaging steps to acquire a plurality of sets of shear wave propagation parameters, the method further comprising a reliability indicator determining step during which a reliability indicator of the shear wave elastography imaging of the observation field is determined.

With these features, the operator can be provided with additional information regarding the reliability of the SWE acquisition/measurement. The operator can thus improve its diagnostic performance by only performing diagnostic and measurements when the shear wave elastography imaging is optimal or by only taking into consideration diagnostic and measurements performed in reliable operating conditions.

In some embodiments, one might also use one or more of the following features:

the reliability indicator is a function of a stability indicator, the reliability indicator determining step comprising a stability indicator determining step during which said stability indicator is determined on the basis of at least two sets of shear wave propagation parameters;

the stability indicator is a function of a similarity between at least two set of data, said two sets of data being two successive sets of shear wave propagation parameters or two histograms respectively associated with two successive sets of shear wave propagation parameters;

the similarity between two set of data is determined by computing a metric for each set of data and comparing said metrics, said metrics being selected in the list of means square, correlation, normalized correlation, pattern intensity and mutual information;

the stability indicator is a function of a statistical dispersion of the plurality of sets of shear wave propagation parameters;

the statistical dispersion of the plurality of sets of shear wave propagation parameters is determined by computing a statistical indicator selected in the list of interquartile range, interdecile range, standard deviation, median absolute deviation, average absolute deviation, distance standard deviation;

the statistical dispersion is determined by further normalizing the computed statistical indicator by a statistical measure of central tendency of the plurality of sets of shear wave propagation parameters;

each shear wave imaging step comprises:

a) an excitation step during which a shear wave is generated inside the medium by causing an array of transducers to emit at least one ultrasound wave into the medium, b) an observation step during which the propagation of said shear wave is observed at a plurality of points in an observation field of the medium,
the observation step comprising the following operations:
b1) causing the array of transducers to emit into the medium a succession of ultrasound waves with spatial coverage and timing adapted so that said ultrasound waves exhibit at least partial spatial and temporal overlap with the propagating shear wave in the observation field, and
b2) causing sound signals received from said observation field to be detected in real time by said array of transducers, said sound signals comprising echoes generated by the ultrasound waves interacting with scatterers in the medium, and c) at least one processing step during which a set of shear wave propagation parameters is determined in the observation field, said set of shear wave propagation parameters being associated with a plurality of points in the observation field;

the reliability indicator is a function of a motion indicator, the reliability indicator determining step comprising a motion indicator determining step during which said motion indicator is determined on the basis of at least two set of data, said two sets of data being two successive B-mode images of the observation field or two successive phase sensitive acquisitions of the observation field, such as Doppler acquisitions;

the motion indicator is a function of a local or global displacement between at least two successive B-mode images determined by computing an optical flow from said two successive B-mode images;

the motion indicator is a function of a local or global displacement between at least two successive phase sensitive acquisitions computed from phase values measurements of said two successive phase sensitive acquisitions;

the reliability indicator is a function of an image quality indicator, the reliability indicator determining step comprising an image quality indicator determining step during which said image quality indicator is determined on the basis of at least one B-mode-image of the observation field;

the image quality indicator is determined by computing a statistical property of at least one B-mode-image, and comparing said statistical property with at least one predefined threshold value;

the statistical property of the plurality of B-mode-images is a B-mode 1st order statistic, a B-mode 2nd order statistic or a combination of B-mode 1st order and 2nd order statistics, of at least one B-mode-image;

the image quality indicator is determined on the basis of at least two B-mode-images of the observation field, the image quality indicator is a function of a similarity between said at least two B-mode-images, said similarity being determined by computing a metric for each of said B-mode images and comparing said metrics, said metrics being selected in the list of means square, correlation, normalized correlation, pattern intensity and mutual information;

the method comprises at least one B-mode imaging step;

the method comprises a plurality of phase sensitive acquisitions steps;

the B-mode imaging steps and/or the phase sensitive acquisition steps are performed before the shear wave imaging steps;

the method further comprises at least one step of comparing a reliability indicator, a stability indicator, a motion indicator and/or an image quality indicator with at least one predefined threshold value;

the method further comprises a step of displaying to an operator a reliability indicator;

the step of displaying to an operator a reliability indicator comprises displaying a stability indicator and/or a motion indicator and/or an image quality indicator;

the step of displaying to an operator the reliability indicator comprises an operation selected from displaying a numerical value of the reliability indicator, and displaying a graphical representation of the reliability indicator;

the method further comprises a step of displaying to an operator a synthetic indicator function of a motion indicator and/or an image quality indicator, said step of displaying a synthetic indicator being performed prior to the plurality of shear wave imaging steps;

a plurality of reliability indicators, associated to a plurality of points in the observation field, are determined, and a map of reliability indicators is displayed to an operator;

said map of reliability indicators comprises a map of stability indicators and/or a map of motion indicators and/or a map of image quality indicators and/or a map of synthetic indicators;

the method comprises a step of determining a composite image on the basis of at least two maps comprising a map of shear wave propagation parameters in the observation field, and the map of reliability indicators, said step of determining a composite image comprising an operation selected from varying a color component of one of said at least two maps in function of another of said at least two maps, alpha blending said at least two maps, determining a set of lines or icons from one of said at least two maps to be layered on top of another of said at least two maps, and a step of displaying to an operator said composite image;

a step of displaying is reiterated several times.

Another object of the invention is an imaging apparatus for implementing a method as detailed above, for shear wave elastography imaging of an observation field in a medium, the apparatus comprising an array of transducers that are controlled independently of one another by at least one electronic central unit adapted to acquire a plurality of sets of shear wave propagation parameters by:

a) causing at least one ultrasound wave to be emitted into the medium by the array of transducers to generate a shear wave inside the medium;

b) observing simultaneously at a plurality of points in an observation field the propagation of said shear wave, by:

b1) causing the array of transducers to emit into the medium a succession of ultrasound waves with spatial coverage and timing adapted so that said ultrasound waves exhibit at least partial spatial and temporal overlap with the propagating shear wave in the observation field; and b2) causing sound signals received from said observation field to be detected in real time by said array of transducers, said sound signals comprising echoes generated by the ultrasound waves interacting with scatterers in the medium; and c) determining a set of shear wave propagation parameters in the observation field, said set of shear wave propagation parameters being associated with the plurality of points in the observation field, to determine a reliability indicator of the shear wave elastography imaging of the observation field.

BRIEF DESCRIPTION OF THE DRAWINGS

Other characteristics and advantages of the invention will readily appear from the following description of its embodiments, provided as non-limitative examples, and of the accompanying drawings.

On the Drawings.

On the different figures, the same reference signs designate like or similar elements.

DETAILED DESCRIPTION

Figure 1:
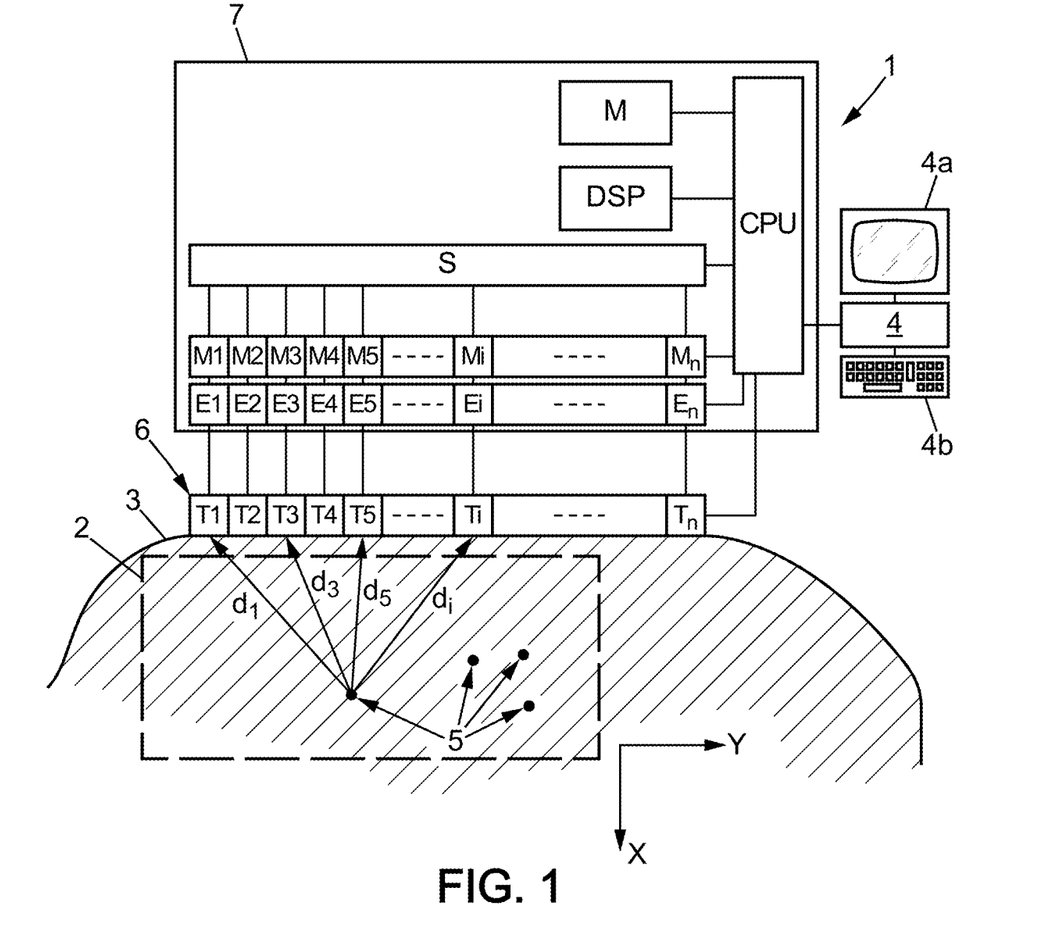
FIG. 1 illustrates an apparatus for performing shear wave elastography imaging of an observation field in a medium according to an embodiment of the invention.

The apparatus 1 shown on FIG. 1 is an ultrasound imaging apparatus adapted for performing a shear wave elastography imaging of an observation field 2 in a medium 3, for instance imaging living tissues and in particular human tissues of a patient.

Apparatus 1 may also be able to perform conventional B-mode imaging and/or phase sensitive acquisitions such as Doppler imaging.

The apparatus 1 may include for instance:

an ultrasound transducer array 6, for instance a linear array typically including a few tens of transducers (for instance 100 to 300) juxtaposed along an axis X as already known in usual echographic probes (the array 6 is then adapted to perform a bidimensional (2D)

imaging of the observation field 2, but the array 6 could also be a bidimensional array adapted to perform a 3D imaging of the observation field 2);

an electronic bay 7 controlling the transducer array and acquiring signals therefrom;

a microcomputer 4 for controlling the electronic bay 7 and viewing ultrasound images obtained from the electronic bay on a display 4a (in a variant, a single electronic device could fulfill all the functionalities of the electronic bay 7 and of the microcomputer 4).

Figure 2:
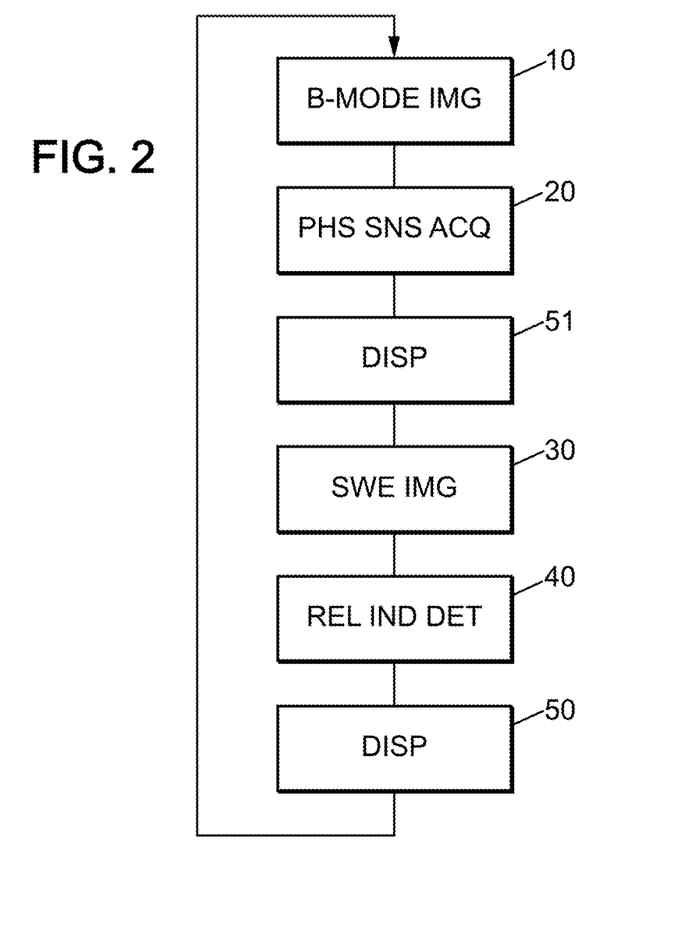
FIG. 2 is a flowchart of a method for performing shear wave elastography imaging of an observation field in a medium according to an embodiment of the invention, FIG. 3 details a shear wave imaging step of a method according to an embodiment of the invention, FIG. 4 details a reliability indicator determining step of a method according to an embodiment of the invention.

As shown on FIG. 2, the electronic bay 7 may include for instance:

n analog/digital converters ($E_1$-$E_n$) individually connected to the n transducers ($T_1$-$T_n$) of the transducer array 6;

n buffer memories ($M_1$-$M_n$) respectively connected to the n analog/digital converters, a central processing unit (CPU) communicating with the buffer memories and the microcomputer 4, a memory (M) connected to the central processing unit;

a digital signal processor (DSP) connected to the central processing unit.

The transducers $T_1$-$T_n$ are controlled independently of one another by the central processing unit. The transducers T1-Tn can thus emit selectively:

either an unfocussed ultrasound wave;

or else an ultrasound wave that is focused on one or more points of the medium 3.

The wording "unfocused ultrasound wave" as understood herein means any unfocused wave illuminating the entire observation field in the medium 3, for instance:

an ultrasound compression wave that is "plane" (i.e. a wave whose wave front is rectilinear in the X,Y plane), or any other type of unfocused wave;

a wave generated by causing random ultrasound signals to be emitted by the various transducers $T_1$-$T_n$;

or an ultrasound compression wave that is focused on one or more points of the medium 3;

or weakly focusing waves (known as "fat" transmit focusing:ratio Focal distance/Aperture>2.5);

or diverging waves such as spherical waves;

or waves focused simultaneously on several focal points;

or more generally any kind of transmit waves that do not correspond to conventional focusing using a single focal point location and a ratio Focal distance/Aperture<2.5.

During operation of the apparatus 1, and in particular the shear wave imaging step 30, the transducer array 6 is for instance placed in contact with a skin of a patient.

The operations of apparatus 1 are controlled by the control system, i.e. the central processing unit (CPU) and/or the computer 4, which are programmed for this way of operation.

Reference will now be made in detail to embodiments of the invention which are described below, by referring to the accompanying figures. In this regards, embodiments of the invention may be embodied in several different forms and should not be construed as being limited to embodiments set forth in the following.

Some embodiments of the invention, hereafter described with reference to flowchart or block diagrams, will be understood as being implementable by computer readable instructions. These computer readable instructions can be provided to a processor of a general purpose computer, a special purpose processor or computer, or other programmable data processing circuit or circuits such that the instructions executed by the processor or circuit create modules that implement the operations and steps specified in the flowcharts blocks.

This way, embodiments of the present invention can be implemented through a non-transitory computer-readable storage device comprising any medium or media permitting the storing and transmission of the computer readable instructions or code.

Figure 3:
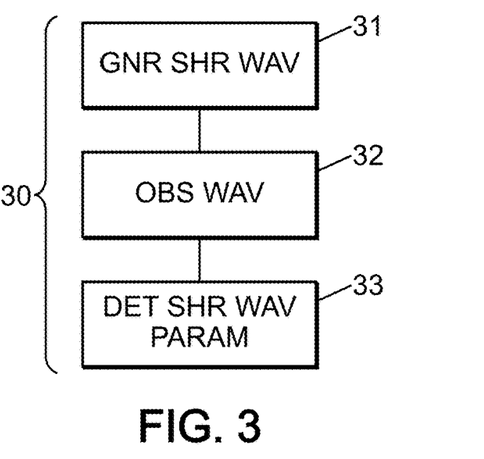

Referring now more particularly to FIGS. 2 and 3, to perform a shear wave imaging step 30, the control system of the apparatus 1 is programmed to perform several steps in succession, as detailed on FIG. 3 and in document U.S. Pat. No. 7,252,004 B2:

a) an excitation step 31 during which the control system causes an shear wave to be generated in the medium 3 by causing at least one ultrasound wave to be emitted by the array 6 (this ultrasound wave may be emitted by all or part of the transducers $T_1$-$T_n$);

b) an observation step 32 during which the propagation of the shear wave is observed at a multitude of points of the observation field; and c) at least one processing step 33 during which the control system processes the successive ultrasound signals received from the observation field 2 during step b) in order to determine shear wave propagation parameters at various points in the observation field.

The ultrasound wave emitted during the excitation step a) 31 may be a monochromatic wave of frequency f lying in the range 0.5 MHz to 15 MHz, for example being equal to about 2.5 MHz, which is emitted for a duration of k/f seconds, where k is an integer lying in the range 50 to 5000 (e.g. being about 500) and f is expressed in Hz. Such a wave may possibly be emitted during a succession of emission periods separated by rest periods, the emission periods following one another at a rate lying in the range 5 to 1000 emissions per second. The shear wave which is thus created propagates parallel to axis Y.

In a variant, the ultrasound wave emitted during excitation step a) is a linear combination (in particular a sum) of two monochromatic signals of respective frequencies f1 and f2 such that 20 Hz≤|f1−f2|≤1000 Hz, thus producing an amplitude modulated wave having a modulation frequency |f1−f2|.

In addition, the ultrasound wave emitted during excitation step a) may optionally be focused simultaneously or otherwise on a plurality of points so that the shear wave as generated presents a desired wave shape (for example it is thus possible to generate a shear wave that is plane, or on the contrary a shear wave that is focused) and illuminates desired zones in the medium 2.

The observation step b) 32 may comprise several steps and in particular a step b1) of emitting a succession of ultrasound waves and a step b2) of detecting in real time echoes from said ultrasound waves.

During step b1), the control system causes the array 6 to emit into the viscoelastic medium a succession of ultrasound waves with spatial coverage and timing adapted so that said ultrasound waves exhibit at least partial spatial and temporal overlap with the propagating shear wave in the observation field. The timing of said ultrasound waves are thus adapted so that at least some of said unfocused ultrasound waves reach the observation field during the propagation of the shear wave through the observation field. Said ultrasound waves may be for instance unfocused ultrasound compression waves emitted by all or part of the transducers $T_1$-$T_n$.

Said ultrasound waves may be emitted at a rate lying in the range 500 to 10,000 shots per second, and preferably in the range 1000 to 5000 shots per second (with this rate being limited by the go-and-return travel time for the compression wave through the patient's body 2: it is necessary for all of the echoes that are generated by the compression wave to have been received by the probe 6 before a new compression wave is sent).

Step b1) may last for example 0.1 to 1 s, it is possible to emit ultrasound compression waves at a rate lying in the range 500 to 10,000 shots per second, and preferably in the range 1000 to 5000 shots per second (with this rate being limited by the go-and-return travel time for the compression wave through the patient's body: it is necessary for all of the echoes that are generated by the compression wave to have been received by the probe 6 before a new compression wave is sent).

Each ultrasound compression wave propagates through the patient's body 2 at a propagation speed that is much higher than that of shear waves (e.g. about 1500 m/s in the human body), and interacts with the reflecting particles 3d, thereby generating echoes or other analogous disturbances in the signal.

During step b2), the control system causes the array 6 to detect ultrasound signals received from patient's body 2. This detection can be carried out by all or part of the transducers of the array 6. The backscattered ultrasound signals comprise echoes generated by the ultrasound waves interacting with scatterers 5 in the observation field. These echoes correspond, directly or indirectly, to successive images of the displacement of the medium in the observation field 2. The detected signals are recorded in real time in the buffer memories $M_1$-$M_n$.

The backscattered signals are picked up by the transducers $T_1$-$T_n$ during step b2), after each shot of an ultrasound compression wave. The signal $s_{ij}$(t) as picked up in this way by each transducer $T_i$ after shot No. j is initially sampled at high frequency (e.g. 30 MHz to 100 MHz) and digitized (e.g. on 12 bits) in real time by the analog/digital converter $E_i$ corresponding to transducer $T_i$.

The signal $s_{ij}$(t) as sampled and digitized in this way is then stored, likewise in real time, in a the buffer memory $M_i$ corresponding to the transducer By way of example, each memory Mi may present a capacity of about 128 megabytes (MB), and contains all of the signals $s_{ij}$(t) received in succession for shots j=1 to p.

As explained in U.S. Pat. No. 7,252,004 B2, after all of the signals $s_{ij}$(t) corresponding to the same propagation of a shear wave have been stored, the central unit 9 processes these signals during step c) to determine shear wave propagation parameters at various points in the observation field.

Processing step c) may comprise a beamforming or pathforming step followed by a step of determination of a displacement to which each scatterer 3 giving rise to an ultrasound echo has been subjected.

Examples of such displacement determination steps are given in U.S. Pat. No. 7,252,004-B2.

This produces a set of displacement vectors $\bar{u}(\bar{r},t)$ generated by the shear waves in each position $\bar{r}$ of the observation field under the effect of the shear wave (these displacement vectors may optionally be reduced to a single component in the example described herein).

This set of displacement vectors is stored in the memory M or in the computer 4 and can be displayed, for example, in particular by means of the screen 4a of the computer 4, in the form of a slow motion picture in which the values of the displacements are illustrated by an optical parameter such as a gray level or a color level.

The propagation differences of the shear wave between zones having different characteristics in the medium 3 can thus be clearly seen.

The motion picture of shear wave propagation can also be superposed on a conventional echographic image, which can also be generated by the apparatus 1 described above.

Furthermore, it is also possible to calculate, instead of displacements, the deformations of the medium 3 for each of the points in the observation field 2, i.e. vectors whose components are the derivatives of the displacement vectors respectively relative to the space variables (X and Y coordinates in the example described). These deformation vectors can be used like the displacement vectors for clearly viewing the propagation of the shear wave in the form of a motion picture, and they also present the advantage of eliminating displacements of the transducer array 6 relative to the patient's body 2 under observation.

From the displacement or deformation fields, the computer 4 (or more generally the control system) can advantageously then compute at least one propagation parameter of the shear wave, either at certain points (at least 1 point) in the observation field as selected by the user acting on the computer 4 using input module 4b, or else throughout the observation field, on the basis of the way in which the movement parameter (displacement or deformation) varies over time in the field of observation X, Y (or X, Y, Z with a two-dimensional array of transducers). When the shear wave propagation parameter is computed at several points in the observation field, the computer 4 may then show a map of said parameter in the observation field, on the screen 4a.

The propagation parameter of the shear wave that is calculated during step c2) is selected, for example, from amongst: the shear modulus µ, or Young's modulus E=3µ, or the propagation speed $c_s$ of shear waves $$(c_s = \sqrt{\frac{E}{3\rho}},$$

where ρ is the density of the tissues), or the shear elasticity µl, as explained in more details in U.S. Pat. No. 7,252,004 B2. Such propagation parameter is representative of the elasticity of medium 3.

This propagation parameter may be computed for instance by the computer 4 (or more generally the control system), repeatedly at several different instants (at least at two different instants $t_1$, $t_2$).

For instance, the control system (e.g. the computer 4) may compute the shear modulus µ(t) of the medium 3 at two different instants $t_1$, $t_2$, e.g. at the systole and at the diastole (respectively at the maximum blood pressure and at the minimum blood pressure).

Thus, one obtains easily, quickly and non-invasively a measurement of elastic properties of the soft tissues. When the shear wave parameters are determined in a plurality of points in the observation field, an image of the shear wave parameters or the elastic properties of the soft tissues (indicated for instance by a scale of colors) may be determined and presented to the user on the computer screen 4a. This image may be superposed to an echography of the patient, obtained through the same apparatus 1, operating for instance in B-mode. The above method works all the more as the shear waves have a relatively high frequency components, e.g. above 50 Hz.

According to the present invention, a method for performing shear wave elastography imaging of an observation field further comprises a reliability indicator determining step 40 during which a reliability indicator of the shear wave elastography imaging of the observation field is determined.

The reliability indicator is representative of the reliability of the acquired shear wave parameters.

In one embodiment of the invention, the reliability indicator is a composite indicator that is function of a stability indicator, a motion indicator and an image quality indicator.

The stability indicator, motion indicator and image quality indicator will be detailed further below but can be generally summarized as follow:

the image quality indicator is representative of the quality of B-mode images obtained from the observation field,
the motion indicator is representative of the motion of living tissues in the observation field, and
the stability indicator is indicative of the temporal stability of the shear wave imaging.

It was discovered by the inventors that these indicators are associated with reliable shear wave acquisitions.

In some embodiment of the invention, the reliability indicator may be only function of one or two indicators of the list consisting of a stability indicator, a motion indicator and an image quality indicator.

In some embodiment of the invention, the reliability indicator is a single numerical or logical value computed from the stability indicator, motion indicator and/or image quality indicator.

In another embodiment, the reliability indicator is a pair or a triplet of numerical or logical values of stability indicator, motion indicator and/or image quality indicator.

The reliability indicator may also be compared with a predefined threshold value, the threshold value being an acceptance threshold, i.e. indicative of a reliability of shear wave acquisitions.

Figure 5A:
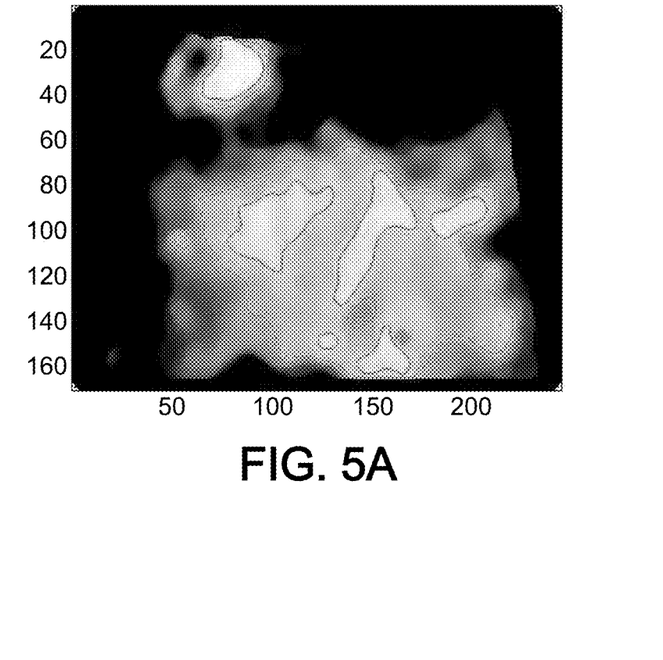
FIG. 5A illustrates a map of reliability indicators with overlaid isolines indicating predefined threshold values of reliability indicators.

FIG. 5A illustrates a map of reliability indicators with several overlaid isolines respectively indicating several predefined threshold values of reliability indicators.

Figure 5B:
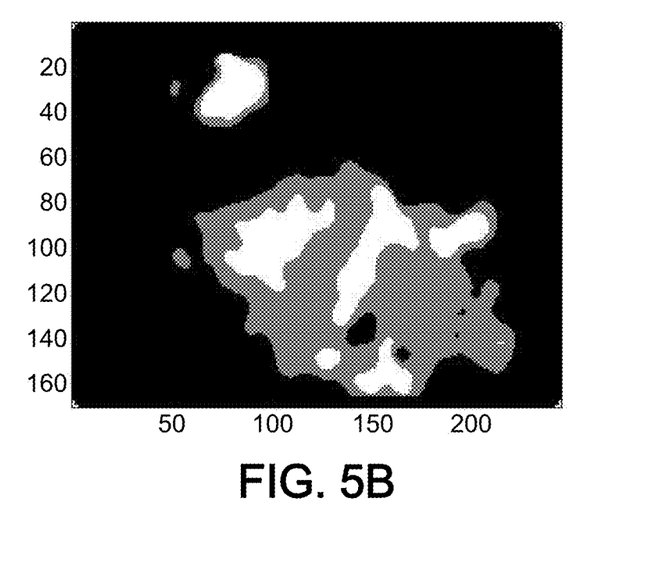
FIG. 5B illustrates a threshold map of threshold values of reliability indicators obtained by comparing the values of reliability indicator illustrated on FIG. 5A with the predefined thresholds also illustrated on FIG. 5A.

FIG. 5B illustrates a threshold map of threshold values of reliability indicators obtained by comparing the values of reliability indicator with the predefined thresholds illustrated on FIG. 5A.

According to a result of said comparison of the reliability indicator with a threshold value, an automatically repeated series of successive shear wave imaging steps 30 may then be stopped by the apparatus 1.

Alternatively, the operator may be informed that a reliable acquisition has been made.

Accordingly, a method according to the invention may further comprise a step of displaying 50 to the operator the reliability indicator.

As illustrated on FIG. 2, the plurality of shear wave imaging steps 30, the step of determining the reliability indicator 40 and the step of displaying 50 may be reiterated several times.

The step of displaying 50 to an operator a reliability indicator comprises displaying a stability indicator and/or a motion indicator and/or an image quality indicator.

Said indicator may be displayed as numerical values or by using a graphical representation, for instance a glyph, a colour icon or a sliding bar.

In one embodiment of the invention, a plurality of reliability indicators is determined and is associated to a plurality of points in the observation field.

Each reliability indicator thus indicates the reliability of a specific pixel of the displayed data.

As illustrated on FIGS. 5A and 5B, a map of reliability indicators can thus be displayed to the operator.

The map of reliability indicators may be restricted to a specific region of interest of the observation, for instance a region of interest that has been selected by the operator.

The map of reliability indicators displayed to the operator may comprise a map of stability indicators, a map of motion indicators and/or a map of image quality indicators.

Said maps may be overlaid one on top of the other in order to be displayed.

In one embodiment of the invention, a composite image may thus be determined and displayed to the operator, said composite image comprising
a map of shear wave propagation parameters in the observation field, and
a map of reliability indicators that may comprises a map of stability indicators, a map of motion indicators and/or a map of image quality indicators.

In this embodiment, the method according to the invention may thus comprise a step of determining such a composite image.

This step may for example be performed by varying a colour component of one of said maps in function of another of said maps, by alpha blending said maps, or by determining a set of lines or icons from at least one of said maps to be layered on top of another of said maps.

Figure 4:
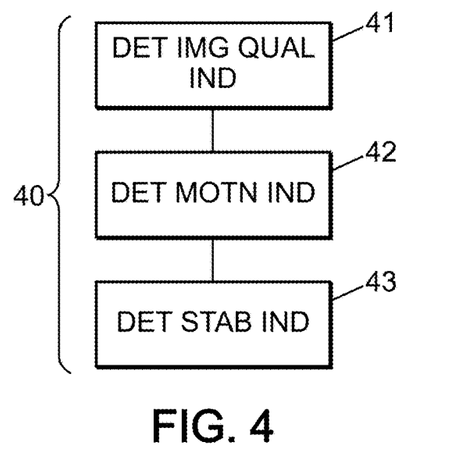

We are referring now more particularly to FIG. 4 which details a reliability indicator determining step according to the invention.

As illustrated on this figure, the stability indicator may be determined during a stability indicator determining step 43 of the reliability indicator determining step 40.

The stability indicator may be determined on the basis of a plurality of sets of shear wave propagation parameters, in particular at least two sets of shear wave propagation parameters.

By a "set of shear wave propagation parameters", it is understood a set of data corresponding to the propagation of a shear wave as generated in step a) in a single shear wave imaging step as detailed above. Thus, said several sets of shear wave propagation parameters respectively correspond to successive, or reiterated, shear wave imaging steps as detailed above, and in particular correspond to the propagation of several associated shear waves.

The number of sets of shear wave propagation parameters, i.e. the number of shear wave imaging steps, can be predefined and can be several shear wave imaging steps, for instance ten shear wave imaging steps or twenty shear wave imaging steps. The stability indicator is then computed on the predefined number of set of shear wave propagation parameters acquired during the same predefined number of shear wave imaging steps.

In a first embodiment of a stability indicator determining step 43 according to the invention, the stability indicator is a function of a similarity between two set of data.

The two sets of data can be two successive sets of shear wave propagation parameters or two histograms respectively associated with two successive sets of shear wave propagation parameters.

More precisely, the similarity between the two sets of data is determined by computing a metric for each set of data and comparing said metrics.

The metric can be means squares, correlations, normalized correlations, pattern intensity, mutual information and the like.

By "means squares", it is meant a sum of squared differences or a sum of absolute differences between data values.

By "correlations" and "normalized correlations", it is meant correlations between data values, optionally divided by the square rooted autocorrelation of both set of data. Such a metric allows comparing sets of data whose data values are related by a linear transformation.

By "pattern Intensity", it is meant squared differences between data values transformed by a function, for instance a function of type 1/(1+x), and summed them up. Such a metric has the advantage of increasing when more data are available and when data values are close.

By "mutual information", it is meant a measure of how much can be known from one set if only the other set is known, as commonly used in information theory. Mutual information may for instance be obtained by subtracting entropy of both sets of data from joint entropy. It thus indicates how much uncertainty about one set is reduced by the knowledge of the second set.

In another embodiment of a stability indicator determining step 43 according to the invention, the stability indicator is a function of a statistical dispersion of the plurality of sets of shear wave propagation parameters.

More precisely, the statistical dispersion of the plurality of sets of shear wave propagation parameters may be determined by computing a statistical indicator that can be for instance interquartile range, interdecile range, standard deviation, median absolute deviation, average absolute deviation, distance standard deviation, or the like.

In one embodiment of the invention, the computed statistical indicator can be further normalized by a statistical measure of central tendency of the plurality of sets of shear wave propagation parameters, such as mean value, median value, mode value, mean of first quartile and third quartile, mean of first decile and last decile, etc.

In one embodiment of the invention illustrated on FIG. 2, the method according to the invention further comprises at least one B-mode imaging step 10, and preferably a plurality of at least two B-mode imaging steps 10.

The B-mode imaging steps 10 may be performed before the plurality of shear wave imaging steps 30.

In this embodiment, the reliability indicator may further be a function of a motion indicator, in particular in addition of being a function of a stability indicator.

The reliability indicator determining step 40 may thus comprise a motion indicator determining step 42 during which a motion indicator is determined on the basis of at least two successive B-mode images of the observation field.

The motion indicator is thus a function of a local or global displacement between two successive B-mode images.

It may in particular be determined by computing an optical flow from said two successive B-mode images.

By "optical flow", it is meant a measure of a displacement of at least a portion of one of said two B-mode images in comparison to the other of said two B-mode images.

By "two successive B-mode images", it is meant that the two B-mode images have not been acquired simultaneously but with a different timing. There is thus a non-zero time interval that separate the moment of acquisition of the two B-mode images. However, the two successive B-mode images don't not need to be consecutive images of a series of B-mode images acquisition and can be separated by several B-mode images of said series.

In one embodiment of the invention, the method according to the invention further comprises a plurality of phase sensitive acquisitions 20 of the observation field 2, such as Doppler acquisitions, an in particular at least two phase sensitive acquisitions 20.

The motion indicator is then a function of a local or global displacement between two successive phase sensitive acquisitions.

The motion indicator may in particular be computed from phase values measurements of said two successive phase sensitive acquisitions.

In one non limitative example of such computation, the phase sensitive acquisitions are pulse inversion acquisition providing Doppler information. A change in pulse inversion Doppler spectra may then be determined for moving tissues and the tissue displacement can be extracted through Doppler processing from either the fundamental or second harmonic components.

Other alternative means of carrying out this computation exist.

In an embodiment of the invention wherein the method comprises a plurality of B-mode imaging steps 10, the reliability indicator may further be a function of an image quality indicator, in addition of being a function of an motion indicator.

The reliability indicator determining step 40 may thus comprise an image quality indicator determining step 41 during which an image quality indicator is determined on the basis of at least one B-mode-image of the observation field 2.

The image quality indicator may in particular be determined by computing a statistical property of the B-mode-image, and comparing said statistical property with a predefined threshold value.

The statistical property of the B-mode-image, or of the plurality of B-mode images, can be in particular:
- a B-mode $1^{st}$ order statistic such as mean, median, etc . . . , or standard deviation, median absolute devation, etc . . . ;
- a B-mode 2nd order statistic, such as co-occurrence matrix, correlation, entropy, etc . . . ;
- or a combination of B-mode $1^{st}$ order and 2nd order statistics.

When the B-mode images represent an ultrasonic speckle field, the speckle brightness or speckle correlation lengths may also be computed as statistical dispersion of the B-mode-image.

Alternatively, the image quality indicator may be a function of a similarity between two B-mode images of a plurality of B-mode images, As detailed above regarding the stability indicator, such a similarity may be determined by computing a metric for each B-mode images and comparing said metrics together. Convenient metrics may for example be a means squares metric, a correlation metric or normalized correlation metric, a pattern intensity metric or a mutual information metric.

The B-mode image or B-mode images may be representative of an ultrasonic speckle field or of the underlying anatomy and tissue echogenicity in the observation field.

It should be noted that while the determination of reliability indicator 40, stability indicator 43, motion indicator 42 and image quality indicator 41, and the imaging steps (B-mode 10, phases sensitive 20 and shear wave 30) have been described above in a specific order, these steps may be performed in differing orders. Of course, the imaging steps required for the determination of a specific indicator are advantageously performed before the determination of said indicator.

Thus, a non limitative example of alternative order for performing the steps of the method according to the invention may be for instance:
1/several B-mode imaging steps 10,
2/a step of determination of image quality indicator 41 and motion indicator 42 from the B-mode images, 3/until a reliability threshold has been reached reiterate the following steps:
  3.1/perform a shear wave imaging step 30,
  3.2/determine a stability indicator 43 and a reliability indicator 40 from the stability indicator, image quality indicator and motion indicator,
  3.3/compare the reliability indicator with the reliability threshold,
  3.4/stop the reiteration if the reliability indicator exceeds the reliability threshold.

Other alternative orders for the steps 10, 20, 30, 40, 50, 31, 32, 33, 41, 42, 43 may exist.

One or several steps of the method may also be performed simultaneously.

In another alternative embodiment of the invention, the method may further comprise an additional step 51 of displaying, prior to performing a shear wave imaging step 30, the image quality indicator and the motion indicator obtained from B-mode images or phase sensitive acquisitions of the observation field.

The step 51 of displaying the image quality indicator and the motion indicator may comprise displaying separately the image quality indicator and the motion indicator, or a map or maps of said indicator. It may also comprise displaying a compound index of the image quality indicator and the motion indicator.

In particular, the step 51 of displaying the image quality indicator and the motion indicator may comprise determining a synthetic indicator function of the image quality indicator and the motion indicator and displaying said synthetic indicator.

By "synthetic indicator" it is meant that the indicator is function of the image quality indicator calculated from B-mode images and function of the motion indicator calculated from B-mode images or from or phase sensitive acquisitions of the observation field.

In one embodiment of the invention, the synthetic indicator, and/or the image quality indicator and/or the motion indicator may be compared with predefined threshold values in a similar way to the above described comparison illustrated on FIGS. 5A and 5B.

The threshold values may be an acceptance threshold, i.e. indicative of a good region B-mode and/or Doppler imaging that has a high probability to lead to high quality shear wave imaging.

Thus, the synthetic indicator may be similar to a clearance sign, displayed on the screen, and indicating to the operator whether he can switch to shear wave imaging.

The synthetic indicator may be computed as the result of a comparison between the predefined threshold values and the image quality indicator and/or the motion indicator.

The synthetic indicator may also be a number or an icon representative of the values of the image quality indicator and/or the motion indicator.

The invention claimed is:

1. A method for performing shear wave elastography imaging of an observation field in a medium, the method comprising:
  acquiring a plurality of sets of shear wave propagation parameters in a plurality of shear wave imaging operations corresponding to respective shear waves, the propagation parameters being one of a shear modulus, Young's modulus, a propagation speed of shear waves, and shear elasticity;
  determining a plurality of reliability indicators of the shear wave elastography imaging operations of the observation field, the plurality of reliability indicators being associated to a plurality of points in the observation field, each of the reliability indicators being determined by a similarity between at least two of the sets of shear wave propagation parameters determined from successive ones of the shear wave elastography imaging operations; and
  displaying to an operator an image of said reliability indicators.

2. The method according to claim 1, wherein each of the reliability indicators is a function of a stability indicator, the reliability indicator determining comprising determining each of the stability indicators based on at least two of the sets of shear wave propagation parameters.

3. The method according to claim 2, wherein each of the stability indicators is a function of the similarity between at least two sets of data, said two sets of data being two successive sets of the shear wave propagation parameters or two histograms respectively associated with two successive sets of the shear wave propagation parameters.

4. The method according to claim 3, wherein the similarity between the two sets of data is determined by computing a metric for each set of data and comparing said computed metrics, said computed metrics being selected from one of means square, correlation, normalized correlation, pattern intensity, and mutual information.

5. The method according to claim 1, wherein each of the stability indicators is a function of a statistical dispersion of the plurality of sets of shear wave propagation parameters.

6. The method according to claim 5, wherein the statistical dispersion of the plurality of sets of shear wave propagation parameters is determined by computing a statistical indicator selected from one of interquartile range, interdecile range, standard deviation, median absolute deviation, average absolute deviation, and distance standard deviation.

7. The method according to claim 6, wherein the statistical dispersion is determined by further normalizing the computed statistical indicator by a statistical measure of central tendency of the plurality of sets of shear wave propagation parameters.

8. The method according to claim 1, wherein the acquiring comprises:
  generating a shear wave inside the medium by causing an array of transducers to emit at least one ultrasound wave into the medium,
  observing the shear wave at a plurality of points in an observation field of the medium, by
    causing the array of transducers to emit into the medium a succession of ultrasound waves with spatial coverage and timing adapted so that said ultrasound waves exhibit at least partial spatial and temporal overlap with the propagating shear wave in the observation field, and
    causing sound signals received from said observation field to be detected in real time by said array of transducers, said sound signals comprising echoes generated by the ultrasound waves interacting with scatterers in the medium; and
  determining the set of shear wave propagation parameters in the observation field, said set of shear wave propagation parameters being associated with a plurality of points in the observation field.

9. The method according to claim 1, wherein the reliability indicators are each a function of a motion indicator, the reliability indicator determining comprising determining the motion indicator based on at least two sets of data, said two sets of data being two successive B-mode images of the observation field or two successive phase sensitive acquisitions of the observation field.

10. The method according to claim 9, wherein the motion indicator is a function of a local or global displacement between two successive B-mode images determined by computing an optical flow from said two successive B-mode images.

11. The method according to claim 9, wherein the motion indicator is a function of a local or global displacement between two successive phase sensitive acquisitions computed from phase values measurements of said two successive phase sensitive acquisitions.

12. The method according to claim 9, wherein the reliability indicators are each a function of an image quality indicator,
the reliability indicator determining comprises determining the quality indicator based on at least one B-mode-image of the observation field.

13. The method according to claim 12, wherein the image quality indicator is determined by computing a statistical property of at least one B-mode-image, and comparing said computed statistical property with a predefined threshold value.

14. The method according to claim 13, wherein the statistical property of the at least one B-mode-image is a B-mode 1st order statistic, a B-mode 2nd order statistic or a combination of B-mode 1st order and 2nd order statistics, of the at least one B-mode-image.

15. The method according to claim 12, wherein the image quality indicator is determined based on at least two B-mode-images of the observation field, and
wherein the image quality indicator is a function of a similarity between said at least two B-mode-images, said similarity being determined by computing a metric for each of said B-mode images and comparing said metrics, said metrics being selected from one of means square, correlation, normalized correlation, pattern intensity, and mutual information.

16. The method according to claim 9, further comprising at least one B-mode imaging operation.

17. The method according to claim 9, further comprising a plurality of phase sensitive acquisitions operations.

18. The method according to claim 16, wherein the B-mode imaging operations and/or the phase sensitive acquisition operations are performed before the acquiring.

19. The method according to claim 1, further comprising at least one of comparing a reliability indicator, a stability indicator, a motion indicator, and/or an image quality indicator with at least one predefined threshold value.

20. The method according to claim 1, wherein the displaying to the operator the image of the reliability indicators comprises displaying one or more of stability indicators, motion indicators, and image quality indicators.

21. The method according to claim 1, wherein the displaying to the operator the image of the reliability indicators comprises one of
displaying numerical values of the reliability indicator, and
displaying a graphical representation of the reliability indicator.

22. The method according to claim 1, further comprising displaying to the operator a synthetic indicator function of a motion indicator, and/or an image quality indicator,
said displaying the synthetic indicator being performed prior to the acquiring.

23. The method according to claim 1, wherein said image of reliability indicators comprises one or more of an image of stability indicators, an image of motion indicators, an image of image quality indicators, and an image of synthetic indicators.

24. The method according to claim 1, further comprising:
determining a composite image based on at least two images comprising
an image of the shear wave propagation parameters in the observation field, and
the image of the reliability indicators,
said determining the composite image comprising one of varying a color component of one of said at least two images in function of another of said at least two images, alpha blending said at least two images, and determining a set of lines or icons from one of said at least two images to be layered on top of another of said at least two images; and
displaying to the operator said composite image.

25. The method according to claim 1, wherein the displaying the image of reliability indicators is reiterated a plurality of times.

26. An imaging apparatus for shear wave elastography imaging of an observation field in a medium, the imaging apparatus comprising:
a display;
at least one electronic central controller; and
an array of transducers that are controlled independently of one another by the at least one electronic central controller configured to:
acquire a plurality of sets of shear wave propagation parameters in a plurality of shear wave imaging operations corresponding to respective shear waves, the propagation parameters being one of a shear modulus, Young's modulus, a propagation speed of the shear waves, and a shear elasticity, by:
causing at least one ultrasound wave to be emitted into the medium by the array of transducers to generate an elastic shear wave inside the medium,
simultaneously observing the propagation of said shear wave at a plurality of points in an observation field, by:
causing the array of transducers to emit into the medium a succession of ultrasound waves with spatial coverage and timing adapted so that said ultrasound waves exhibit at least partial spatial and temporal overlap with the propagating shear wave in the observation field, and
causing sound signals received from said observation field to be detected in real time by said array of transducers, said sound signals comprising echoes generated by the ultrasound waves interacting with scatterers in the medium, and
determining the plurality of sets of shear wave propagation parameters in the observation field, said set of shear wave propagation parameters being associated with the plurality of points in the observation field, and
determine a plurality of reliability indicators of the shear wave elastography imaging operations of the observation field, said plurality of reliability indicators being associated to a plurality of points in the observation field, each of the reliability indicators being determined by a similarity between at least two of the sets of shear wave propagation parameters determined from successive ones of the shear wave elastography imaging operations, and display, on the display to an operator, an image of said plurality of reliability indicators.

* * * * *